United States Patent [19]

Robertson

[11] 4,007,271
[45] Feb. 8, 1977

[54] DERMATALOGICAL COMPOUNDS AND COMPOSITIONS

[75] Inventor: Andrew Robertson, Newcastle-upon-Tyne, England

[73] Assignee: Sterling Drug Inc., New York, N.Y.

[22] Filed: May 21, 1976

[21] Appl. No.: 688,616

Related U.S. Application Data

[63] Continuation-in-part of Ser. No. 449,539, March 8, 1974, abandoned, which is a continuation-in-part of Ser. No. 308,261, Nov. 20, 1972, abandoned.

[30] Foreign Application Priority Data

Nov. 26, 1971 United Kingdom ............ 54927/71

[52] U.S. Cl. .............................. 424/234; 260/351; 260/476 C; 424/242; 424/308; 424/309
[51] Int. Cl.² ........................................ C07C 69/78
[58] Field of Search ......... 424/234, 308, 309, 242; 260/351, 476 C

[56] References Cited

UNITED STATES PATENTS 1,935,928  11/1933  Zahn ................................ 260/351

OTHER PUBLICATIONS

Schultz, Chem. Abstracts, 45 (1951) Col. 7751b.

*Primary Examiner*—Arthur P. Demers
*Attorney, Agent, or Firm*—Paul E. Dupont; B. Woodrow Wyatt

[57] ABSTRACT

Mono-, di- or tri-(X,Y-substituted-benzoyl) esters of 1,8,9-trihydroxyanthracene, wherein the anthracene moiety can be substituted by methyl at the 3-position, X is halogen, hydroxy, nitro, lower-alkyl, lower-alkoxy, phenoxy, trifluoromethyl, lower-alkylcarboxy or lower-alkoxycarbonyl and Y is hydrogen or has the meaning given hereinabove for X, are prepared by reacting the appropriate 1,8,9-trihydroxyanthracene with the appropriate substituted-benzoic acid or functional derivative thereof, e.g., acid chloride, in an inert solvent, in the presence of a suitable basic catalyst, e.g., pyridine or triethylamine, and under an inert atmosphere. Pharmaceutical compositions comprising these esters are useful in treating dermatological conditions such as psoriasis and have the improvements of having substantially no undesirable staining and irritating properties.

37 Claims, No Drawings

DERMATALOGICAL COMPOUNDS AND COMPOSITIONS

COMPOSITIONS AND METHOD

This application is a continuation-in-part of copending application Ser. No. 449,539, filed Mar. 8, 1974 now abandoned which is in turn a continuation-in-part of application Ser. No. 308,261, filed Nov. 20, 1972, now abandoned.

This invention relates to novel anthracene derivatives, to pharmaceutical compositions incorporating them, and to a method of using the same for treating inflammatory conditions of the skin, especially psoriasis. In particular, the invention concerns novel derivatives of 1,8,9-trihydroxyanthracene which are of use in human or in veterinary medicine.

1,8,9-Trihydroxyanthracene, which, in its tautomeric form - 1,8-dihydroxy-9-anthrone — is commonly known as "dithranol" (see the British Pharmaceutical Codex, 1968), has for many years been one of the most successful pharmaceuticals employed in treating dermatological conditions such as psoriasis, as has the related compound 1,8,9-trihydroxy-3-methyl-anthracene (commonly known as "chrysarobin") which is described in the Merck Index as a mixture of 1,8,9-trihydroxy-3-methyl-anthracene and its tautomer 1,8-dihydroxy3-methyl-9-anthrone). Unfortunately, however, the use of dithranol or chrysarobin has a number of quite serious disadvantages, not the least of which is that each can result in severe staining and irritation of the skin. We have now found that certain ester-type derivatives of these compounds have no, or substantially no, such staining and irritating properties, while retaining the desired pharmaceutical activity.

In one aspect, therefore, this invention provides the substituted-benzoyl esters of 1,8,9-trihydroxyanthracenes.

These esters may, of course, be the mono-, di- or tri-(substituted-benzoyloxy)anthracenes, and the anthracene moiety may of course itself bear substituents (especially a methyl group at the 3-position).

The benzoyloxyanthracenes of the invention are those falling within the general formula I:

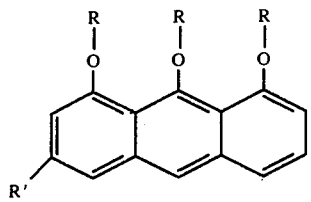

wherein:
each R is a hydrogen atom or an X,Y-substituted-benzoyl group, at least one R being an X,Y-substituted-benzoyl group;
X is a halogen atom, hydroxy, nitro, lower-alkyl, lower-alkoxy, phenoxy, trifluoromethyl, lower-alkylcarboxy or lower-alkoxycarbonyl;
Y is a hydrogen atom or has the meaning given hereinabove for X, and
R' is a hydrogen atom or a methyl group.

If no, one or two groups R represent a hydrogen atom, then the compounds are tri-, di- or mono-benzoyloxyanthracenes respectively.

A preferred group of compounds within that of general formula I is the group wherein each R is an X,Y—substituted-benzoyl group, and R' is a hydrogen atom — thus, the tri-benzoyl esters of dithranol itself.

As used hereinabove and throughout the specification and claims the terms "lower-alkyl" and "lower-alkoxy" designate alkyl and alkoxy groups having from one to four carbon atoms arranged as straight or branched chains illustrated by but not limited to methyl, ethyl, isopropyl, tert-butyl and the like for lower-alkyl; and methoxy, ethoxy, isopropoxy, tert-butoxy and the like for lower-alkoxy. The terms lower-alkylcarboxy and lower-alkoxycarbonyl designate alkylcarboxy and alkoxycarbonyl groups wherein the respective alkyl and alkoxy moieties are lower-alkyl and lower-alkoxy as defined hereinabove.

In the compounds of this invention:
when X or Y represents a halogen atom, it is preferably chlorine;
when X or Y represents a lower-alkyl group, it is preferably the methyl group;
when X or Y represents a lower-alkoxy group, it is preferably the methoxy group;
when X or Y represents a lower-alkylcarboxy group, the lower-alkyl moiety thereof is preferably the methyl group; and,
when X or Y represents a lower-alkoxycarbonyl group, the lower-alkoxy moiety thereof is preferably a methoxy group.

The substituents X and Y can be at any position in the phenyl ring of the benzoyl group.

Two particularly preferred compounds of the invention are:
1,8,9-tri(2-hydroxybenzoyloxy)anthracene (trisalicyloyldithranol); and
1,8,9-tri(2-acetoxybenzoyloxy)anthracene (tri-2-acetoxybenzoyldithranol).

Other preferred compounds of the invention are:

1,8,9-tri(4-chlorobenzoyloxy)anthracene;
1,8,9-tri(3-chlorobenzoyloxy)anthracene;
1,8,9-tri(2-chlorobenzoyloxy)anthracene;
1,8,9-tri(4-methylbenzoyloxy)anthracene;
1,8,9-tri(3-methylbenzoyloxy)anthracene;
1,8,9-tri(4-nitrobenzoyloxy)anthracene;
1,8,9-tri(3-nitrobenzoyloxy)anthracene;
1,8,9-tri(4-methoxybenzoyloxy)anthracene;
1,8,9-tri(4-hydroxybenzoyloxy)anthracene;
1,8,9-tri(2-phenoxybenzoyloxy)anthracene;
1,8,9-tri[3-(trifluoromethyl)benzoyloxy]anthracene;
1,8,9-tri[4-(methoxycarbonyl)benzoyloxy]anthracene;
1,8,9-tri(2-hydroxybenzoyloxy)-3-methyl-anthracene;
and the mono- and di(2-acetoxybenzoyl) esters of 1,8,9-trihydroxyanthracene.

The compounds of this invention can be prepared by conventional methods adopted for the esterification of phenols. Thus, in general the compounds can be prepared by reacting the appropriate 1,8,9-trihydroxyanthracene with the appropriate substituted benzoic acid (or functional derivative thereof), in an inert solvent, in the presence of a catalyst, and under an inert atmosphere.

The reaction is most conveniently carried out using, as the benzoic derivative, a benzoyl halide, preferably the appropriate substituted benzoyl chloride and a basic catalyst, though other derivatives — for example, the anhydride — can be used.

If the triester is to be prepared, then advantageously the benzoyl derivative is used in excess of the three molar equivalents stoichiometrically required; at least 1.25 times as much — thus, 3.75 molar equivalents - is desirable, and preferably a little more still is employed (in order to allow for wastage due to side reactions). However, if a mono- or di-ester product is to be prepared, then the benzoyl derivative should be used in approximately the quantity required stoichiometrically — i.e. approximately one or two molar equivalents, as appropriate. Inevitably in these cases a mixture of products will result (unchanged starting material, monoester, diester and triester), and these will need to be separated by conventional separation techniques (for example, chromatographic methods). A preferred preparative technique is to use approximately two molar equivalents of the benzoyl halide, and to isolate the mono- and diesters that are formed from the resulting reaction mixture.

The inert solvent can be an aromatic hydrocarbon, for example benzene, toluene or xylene (the last two are particularly preferred), or it can be an alkyl fatty acid ester, for example ethyl acetate or (preferably) isopropyl acetate.

The basic catalyst is desirably one of moderate strength. Nitrogenous bases are generally suitable, particularly heterocylic materials (such as pyridine) and tertiary amines (such as trimethylamine or triethylamine).

The reaction should be effected under an inert atmosphere to avoid oxidation by-products being formed. A suitable atmosphere is nitrogen, though other inert gases — argon, for example — can be employed.

The rate of reaction is, of course, temperature dependent. Preferably the reaction is carried out at a temperature in the range of from room temperature (about 15° C.) to 60° C.; below this range the reaction is very slow, while above the range there is a serious tendency for sidereactions to take predominance, so that the purity of the desired product suffers.

It is highly desirable that any benzoyl chloride reagent be as pure as possible. Not only do impurities reduce the available quantity of the reagent itself, but they tend to take part in side-reactions resulting in a very impure product. A contaminant especially to be avoided is thionyl chloride (employed in the manufacture of benzoyl chlorides), which complexes with the basic catalyst.

The product obtained by the above-described process can in general be isolated from the reaction mixture, and purified, by conventional methods. Isolation and purification can thus be effected either by crystallisation from a suitable solvent, or by precipitation from solution using petroluem spirit or a hydrocarbon such as n-hexane. A suitable solvent for crystallisation is a mixture of toluene and dimethylformamide (ratios from 90:10 to 50:50 are suitable), and suitable solvents for the isolation by precipitation are either aliphatic esters (such as isopropyl acetate) or arenes (such as benzene, toluene or xylene).

As stated above, the anthracene derivatives of the invention are useful in medicine for the treatment of inflammatory conditions of the skin, and are especially effective in causing the temporary remission of psoriatic lesions.

However, before any of these compounds may be used in medicine, they should preferably be formed into pharmaceutical compositions by association with suitable pharmaceutical vehicles.

The term "pharmaceutical" is used herein to exclude any possibility that the nature of the vehicle, considered of course, in relation to the route by which the composition is intended to be administered, could be harmful rather than beneficial. The choice of a suitable mode of presentation, together with an appropriate vehicle, is believed to be within the competence of those accustomed to the preparation of pharmaceutical formulations.

Accordingly, in yet another aspect, this invention provides pharmaceutical compositions containing one or more benzoyloxyanthracenes of the invention, in association with a suitable pharmaceutical vehicle.

The compositions of this invention are primarily for administration topically, and in respect of this mode the "pharmaceutical vehicle" is preferably the solid or liquid carrier of a dusting powder, ointment, cream, lotion, skin-tonic, salve, unguent or paste.

In general, the compositions of this invention will contain from 0.05% to 10%, especially 0.1% to 10%, by weight of the active anthracene derivative.

Most preferably the topical compositions are in the form of a paste or cream, and can contain other therapeutic agents of value in the topical treatment of dermatological conditions, in addition to the anthracene derivative. Suitable agents for inclusion are keratolytic agents (such as salicylic acid), or corticosteroid compounds (such as hydrocortisone).

The following Examples and Test results are now given, though only by way of illustration, to show details of reagents, reaction conditions and techniques, and compositions, of the invention.

The 1,8,9-trihydroxyanthracenes used in these Examples were in fact mostly in the form of the 1,8-dihydroxy-9-anthrone tautomers.

EXAMPLE 1

Preparation of 1,8,9-tri(2-acetoxybenzoyloxy)-anthracene 1,8,9-Trihydroxyanthracene (113 g.), triethylamine (151.5 g.), and isopropyl acetate (1 liter) were stirred together at room temperature under nitrogen. 2-Acetoxybenzoyl chloride (400 g.) was added dropwise during forty-five minutes, and the mixture was stirred for a further thirty minutes, and then filtered. The filtrate was added slowly, with vigorous stirring, to light petroleum (b.p. 40°–60° C., 8 liters), and the precipitated solid was washed well with light petroleum (b.p. 40°–60° C.) and then dissolved in boiling isopropyl acetate (1 liter). The solution was charcoaled, filtered through a "Celite" bed, and allowed to cool, and the cold solution was filtered and added slowly, with vigorous stirring, to light petroleum (b.p. 40°–60° C., 8 liters). The precipitated solid (210 g.) was subjected to this procedure a second time to yield 1,8,9-tri(2-acetoxybenzoyloxy)anthracene (158 g., 44%), m.p. 105°–120° C. (decomp.).

The following points are important for a good yield.

1. The precipitations must be done slowly, to avoid the formation of oily lumps.

2. The precipitated solid must be well washed with light petroleum (b.p. 40°–60° C.), in order to prevent spontaneous decomposition.

3. It is essential to add the precipitated solid to boiling isopropyl acetate in order to prevent tar formation.

EXAMPLE 2

Alternative preparation of 1,8,9-tri(2-acetoxybenzoyloxy)anthracene 1,8,9-Trihydroxyanthracene (120 g.) was heated in xylene (1200 g.) and pyridine (300 g.) for ten minutes at 60° C. under a constant stream of nitrogen. 675 g. Of 2-acetoxybenzoyl chloride (acetylsalicyloyl chloride) were added dropwise over fifteen minutes with vigorous stirring, maintaining the temperature at 60° C. throughout. After a further ten minutes at 60° C., the dark green solution was poured into a large excess of petroleum spirit (5 liters, b.p. 40°–60° c.) with rapid stirring, when a yellow green solid precipitated out.

The precipitate was washed well with diethyl ether, and dried at room temperature to give 320 g. of crude product (85% yield), decomposing above 145° C.

The crude product was added, in portions of 50 g., to boiling xylene (300 ml.) and decolourising charcoal. The solution was filtered through a diatomaceous earth ("Celite") bed to give a dark yellow solution; this was added when cold to petroleum spirit (500 ml., b.p. 40°–60° C.). Filtration gave a purified product as a pale yellow amorphous solid (30 g. — yield 60%), decomposing at 152° C. The overall yield for the preparation was 50%.

The product was characterized by the following methods:

1. Mircroanalysis
$C_{41}H_{28}O_{12} = 712$
Calculated:C%, 69.10; H%, 3.96. Found: C%, 69.26; H%, 4.09.

2. Mass Spectrometry
The molecular ion was shown to be M = 712

3. Chromatography
Thin layer chromatography, using various solvent systems (chloroform/methanol — 90/10; toluene; and ethyl acetate/ethanol — 755/25), showed the product to be a single entity.

4. I.R. Spectrum (KBr disc)
1750 cm$^{-1}$ — C=O (of aromatic ester and acetylated phenol)
1610 cm$^{-1}$ — C=C (aromatic)
1370 cm$^{-1}$ — C-H (of acetyl C-CH$_3$)
1245 cm$^{-1}$ — C-O (of aromatic ester)
1200 cm$^{-1}$ — C-O (of acetylated phenol)

5. N.M.R. Spectrum (Deuterochloroform)
Tau values were: 7.8–7.7 (9H, s, 3 x COCH$_3$) 3.4–1.4 (19H, m, aromatics)

The following points are important for the production of high yields.

a. The acetylsalicyloyl chloride (2-acetoxybenzoyl chloride) was obtained by the reaction of acetylsalicyclic acid (2-acetoxybenzoic acid) and thionyl chloride in chloroform in the presence of aluminum chloride. It was found essential that this product was fully purified (under vacuum) to free it from all thionyl chloride (which complexes with pyridine, causing a severe reduction in yield).

b. The reaction was carried out under nitrogen to prevent formation of a purple oxidation product which decomposed on standing.

c. The reaction product must be worked up immediately.

d. Vigorous stirring of the initial reaction and subsequent precipitation was essential to prevent formation of an intractable tar.

e. Thorough washing of the precipitated material with diethyl ether was essential to remove pyridine and/or xylene, thus preventing tar formation.

Note

The melting point observed for this compound is of no great significance, since the product begins to decompose at temperatures well below that at which the compound melts, and in general it is found that the larger the batch size the wider the decomposition/melting range of the product.

EXAMPLE 3

Preparation of 1,8,9-tri(2-hydroxybenzoyloxy)anthracene 1,8,9-Trihydroxyanthracene (72 g.) was suspended in toluene (800 ml.), and the mixture was heated to 50° C. under a nitrogen atmosphere while pyridine was added (180 ml.). When the phenol was dissolved, the temperature was reduced to 30° C., and salicyloyl chloride (200 g., 4 eq.) was added dropwise. The pyridinium salt (hydrochloride) immediately precipitated, the mixture was stirred for a further five minutes, and the pyridinium salt was removed by filtration.

The toluene solution remaining was added slowly to petroleum spirit (9 liters, b.p. 40°–60° C.) to precipitate the crude ester product, which was filtered off and partially dried by suction.

The crude ester was dissolved in toluene (500 ml.), activated charcoal was added, and the mixture was filtered through a diatomaceous earth ("Celite") bed. The ester was reprecipitated by addition to petroleum spirit (9 liters, b.p. 40°–60° C.). The precipitated ester was partially dried by filtration, added to ether (400 ml.), and the ethereal mixture was stirred for one hour and then filtered. The ester was collected and air-dried on filter paper.

The purified product was a pale yellow amorphous solid (60 g., 32%), m.p. 122° C. (decomp.).

Purification was best carried out on a small scale (use of large quantities gave a dark green tar which solidified slowly to a brittle, green amorphous solid).

1. Microanalysis
$C_{35}H_{22}O_9 = 586$ Calculated: C,% 71.7; H%, 3.8. Found: C,% 71.4, H%, 3.4.

2. Mass Spectrometry
Careful control of the operating conditions identified the molecular ion as m/e = 586

3. Chromatography
Thin layer chromatography, using various solvents (chloroform/methanol — 90/10; toluene; and ethyl acetate/ethanol — 75/25) showed the product to be pure.

4. I.R. Spectrum (KBr disc):
3250 cm$^{-1}$ — OH (salicyloyl)
1750 cm$^{-1}$ — C=O (ester)
1610 cm$^{-1}$ — C=C (aromatic)
1245 cm$^{-1}$ — C—O (ester)
750, 695 cm$^{-1}$ — C—H (aromatic)

The salicyloyl chloride required for this preparation was obtained from the reaction of salicylic acid and thionyl chloride in petroleum spirit (b.p. 40°–60° C.) in the presence of pyridine (100% yield).

EXAMPLE 4

Preparation of 1,8,9-tri(4-chlorobenzoyloxy)anthracene 1,8,9-Trihydroxyanthracene (8 g.), benzene (250 ml.), and pyridine (24 g.) were stirred together at ambient temperature under a stream of nitrogen until a clear solution was obtained. 4-Chlorobenzoyl chloride (25 g.) was added over fifteen minutes, and the formed solution was heated under reflux for 3 hours. The solvent was then removed under reduced pressure, ethanol (200 ml.) was added, and the pale yellow precipitate produced was heated under reflux in ethanol (500 ml.), filtered hot, and the residue washed with ethanol, and dried. Crystallisation from toluene/dimethylformamide (80/20) gave the ester as pale yellow needles (12.8 g., 56%) m.p. 314° C. (decomp.).

EXAMPLE 5

Preparation of 1,8,9-tri(3-chlorobenzoyloxy)anthracene

This ester was prepared in a manner similar to that used for 1,8,9-tri(4-chlorobenzoyloxy)anthracene in Example 4.

Crystallisation from toluene/dimethylformamide (75/25) gave the ester as pale yellow needles (9 g., 40%) m.p. 276°–277° C.

EXAMPLE 6

Preparation of 1,8,9-tri(2-chlorobenzoyloxy)anthracene

This ester was prepared in a manner similar to that used for 1,8,9-tri(4-chlorobenzoyloxy)anthracene in Example 4.

Crystallisation from toluene/dimethylformamide (90/10) gave the ester as pale yellow needles (13 g., 57%) m.p. 272°–273° C.

EXAMPLE 7

Preparation of 1,8,9-tri(4-methylbenzoyloxy)anthracene 1,8,9-Trihydroxyanthracene (8 g.), benzene (250 ml.), and pyridine (24 g.) were stirred together at ambient temperature under a stream of nitrogen until a clear solution was obtained. 4-Methylbenzoyl cloride (25 g.) was added over five minutes, and the solution was heated under reflux for three hours. The solvent was then removed under reduced pressure, ethanol (200 ml.) added, and the pale yellow precipitate produced was heated under reflux in ethanol (500 ml.), filtered hot, and the residue washed with ethanol and dried. Crystallisation from toluene/dimethylformamide (90/10) gave the ester as pale yellow needles (3 g., 15%) m.p. 269° C. (decomp.).

EXAMPLE 8

Preparation of 1,8,9-tri(3-methylbenzoyloxy)anthracene

This ester was prepared in a manner similar to that used for 1,8,9-tri(4-methylbenzoyloxy)anthracene in Example 7.

Crystallisation from toluene/dimethylformamide (80/20) gave the ester as pale yellow needles (13 g., 60%) m.p. 258°–260° C.

EXAMPLE 9

Preparation of 1,8,9-tri(4-nitrobenzoyloxy)anthracene 1,8,9-Trihydroxyanthracene (8 g.), benzene (250 ml.), and pyridine (24 g.) were heated under reflux under a stream of nitrogen until a clear solution was obtained (about five minutes). 4-Nitrobenzoyl chloride (25 g.) was added over ten minutes, and the refluxing was continued for a further two hours. The solvent was then removed under reduced pressure, ethanol added (200 ml.), and the yellow brown precipitate produced was heated under reflux with ethanol (500 ml.), filtered hot, and the residue washed with ethanol. Crystallisation from dimethylformamide/toluene (50/50) gave the ester as straw coloured needles (1.5 g., 6%) m.p. 165° C. (decomp.).

EXAMPLE 10

Preparation of 1,8,9-tri(3-nitrobenzoyloxy)anthracene 1,8,9-Trihydroxyanthracene (8 g.), benzene (250 ml.), and pyridine (24 g.) were heated under reflux under a stream of nitrogen until a clear solution was obtained (about five minutes). 3-Nitrobenzoyl chloride (25 g.) was added over ten minutes, and the refluxing was continued for a further six hours. The solvent was then removed under reduced pressure, ethanol added (200 ml.), and the brown precipitate produced was heated under reflux in ethanol (500 ml.), filtered hot, and the residue washed with ethanol. Crystallisation from toluene/dimethylformamide (90/10) gave the ester as a pale brown amorphous solid (3.5 g., 14%) m.p. 265° C. (decomp.).

EXAMPLE 11

Preparation of 1,8,9-tri(4-methoxybenzoyloxy)-anthracene 1,8,9-Trihydroxyanthracene (8 g.), benzene (250 ml.), and pyridine (24 g.) were stirred together at ambient temperature under a stream of nitrogen until a clear solution was obtained. 4-Methoxybenzoyl chloride (25 g.) was added over five minutes, and the solution heated under reflux for three hours. The solvent was then removed under reduced pressure, ethanol (200 ml.) added, and the pale yellow precipitate produced was heated under reflux with ethanol (500 ml.), filtered hot, and the residue washed with ethanol and dried. Crystallisation from toluene/dimethylformamide (90/10) gave the ester as pale yellow needles (11 g., 50%) m.p. 260° c. (decomp.).

EXAMPLE 12

Preparation of 1,8,9-tri(4-hydroxybenzoyloxy)anthracene 1,8,9-Trihydroxyanthracene(8 g.), benzene (250 ml.), and pyridine (24 g.) were stirred together at ambient temperature under a stream of nitrogen until a clear solution was obtained. 4-Hydroxybenzoyl chloride (25 g. — obtained from 4-hydroxybenzoic acid/thionyl chloride) was added over fifteen minutes, and stirring continued for 1 hour. A dark brown tarry material was obtained, and this was washed well with ethanol and dissolved in boiling toluene/dimethylformamide (90/10). Cooling gave a pale green/brown solid, which was crystallised from toluene/dimethylformamide (90/10) to give the ester as pale green needles (0.5 g., 2%) m.p. 227° C. (decomp.).

EXAMPLE 13

Preparation of
3-methyl-1,8,9-tri(2-hydroxybenzoyloxy)anthracene 1,8,9-Trihydroxy-3-methyl-anthracene (chrysarobin - 8 g.) was suspended in toluene (200 ml.), and heated to 50° C. on a water bath under a constant stream of nitrogen. Pyridine (20 ml.) was added, and the mixture stirred until all the phenol had dissolved. The temperature was then reduced to 30° C., and salicyloyl chloride (25 g.) was added dropwise over ten minutes. The mixture was heated under reflux for 3 hours, and then concentrated under reduced pressure. Addition of ethanol gave a yellow brown tarry mass, which was washed with boiling ethanol, dissolved in boiling toluene, charcoaled, and filtered. The filtrate was added dropwise to petroleum spirit (40°–60° C.) with vigorous stirring, and the precipitate filtered off to give the purified ester as a pale yellow solid (12 g., 60%) m.p. 160° C. (decomp.).

EXAMPLE 14

Preparation of the mono- and di-(2-acetoxybenzoyl) esters of 1,8,9-trihydroxyanthracene 1. Preparation of a mixture of the esters 1,8,9-Trihydroxyanthracene (6 g.), xylene (60 g.), and pyridine (5 g.) were stirred under nitrogen for ten minutes at 60° C. 2-Acetoxybenzoyl chloride (10.5 g., 2 mol. equivs.) was added dropwise over five minutes, and after a further ten minutes heating was discontinued. Charcoal and "Celite" were added, and stirring was continued for ten minutes. The mixture was filtered through "Celite", and the filtrate was added dropwise to stirred petroleum spirit (b.p. 40°–60° C., 750 ml.). The product was isolated as a pale green amorphous solid (4 g.).

Examination of the product by thin layer chromatography showed the presence of only a small proportion of free 1,8,9-trihydroxyanthracene. Spots indicating the presence of lower esters were observed, in addition to the spot corresponding in position to that of the tri-ester.

A similar preparation was performed using only one molecular equivalent of the 2-acetoxybenzoyl chloride and of pyridine to one equivalent of 1,8,9-trihydroxyanthracene. In this case, the yellow-brown product was found to contain a relatively large proportion of free 1,8,9-trihydroxyanthracene, and was considered to be less suitable for further separation procedures than the previously described product.

2. Separation of the esters by dry column chromatography

The separation was performed on 1 g. of material, which was dissolved in chloroform (50 ml.), added to silica gel (Woelm, for dry column chromatography, 15 g.), and the solvent evaporated under reduced pressure. The resulting dispersion of mixed esters on silica gel was applied to a dry column (3 × 50 cm.), and eluted with toluene.

The resulting seven distinct, coloured bands were physically separated, eluted with chloroform through sintered glass, and the resulting solutions were examined by thin layer chromatography.

Samples 5, 6 and 7 were the major samples, and these were evaporated to dryness, and the solid products obtained from these samples were examined by mass spectrometry and shown to be the mono-ester, the di-ester and the tri-ester, respectively.

(The samples were numbered from 1–7 in decreasing order of Rf values.)

EXAMPLE 14a

Preparation of 1,8-di-(4-toluoyloxy)-9-anthrone 1,8,9-Trihydroxyanthracene (8 g.), benzene (250 ml.), and pyridine (24 g.) were stirred together at ambient temperature under a stream of nitrogen until a clear solution was obtained. Then 4-toluyl chloride (25 g.) was added over 5 minutes and the solution heated under reflux for 4 hours. The solvent was removed under reduced pressure and ethanol (200 ml.) added. The yellow precipitate produced was filtered, washed well with ethanol and ether, and dried (50°/0.1 mm./24 hr.). Crystallization from toluene/dimethylformamide (80/20) gave the ester as yellow crystals (10.9 g., 67%), m.p. 252° C. (dec.).

EXAMPLE 14b

Preparation of
1,8,9-tri-(2,4-dichlorobenzoyloxy)anthracene 1,8,9-Trihydroxyanthracene (8 g.), benzene (250 ml.), and pyridine (48 g.) were stirred together at ambient temperature under a stream of nitrogen until a clear solution was obtained. Then 2,4-dichlorobenzoyl chloride (25 g.) was added over 15 minutes and the solution heated under reflux for 9 hours. The solvent was removed under reduced pressure, ethanol (250 ml.) added and the yellow precipitate produced was filtered. The solid was well washed with water, ethanol and finally ether, and dried in vauco at ambient temperature to give the triester (15.7 g., 59.5%). Crystallization from toluene/dimethylformamide (75/25) gave the ester as a yellowgreen crystalline solid (10.3 g., 39%), m.p. 305° C. (dec.).

EXAMPLE 15

1,8,9-Tri(2-phenoxybenzoyloxy)anthracene 1,8,9-Trihydroxyanthracene (4 g.), benzene (125 ml.) and pyridine (12 g.) were stirred under nitrogen until a clear solution resulted. 2-Phenoxybenzoyl chloride (17 g.) was added and the mixture was stirred for 2 hours, filtered and evaporated under reduced pressure to a thick oil. This was dissolved in toluene and the solution was added dropwise with stirring to petroleum ether (b.p. 40°–60° C.) to yield a pale yellow-green solid (13 g., 90%), m.p. 110° C.

EXAMPLE 16

1,8,9-Tri(3-trifluoromethylbenzoyloxy)anthracene 1,8,9-Trihydroxyanthracene (1 g.), benzene (30 ml.) and pyridine (3 g.) were stirred under nitrogen to produce a clear solution and 3-trifluoromethylbenzoyl chloride (4 g.) was added dropwise. After stirring for 1 hour the mixture was filtered and the filtrate was evaporated under reduced pressure to an oil. This was dissolved in ethanol and added dropwise with stirring to water to precipitate a yellow solid (3.0 g., 92%).

A sample of the product (0.8 g.) was adsorbed on silica gel (10 g.) and subjected to dry column chromatography (Woelm silica gel for dry column chromatography 20 × 1 in.). The leading component was eluted with methanol and evaporated to give a yellow solid, m.p. 125° C. which was characterized by the usual techniques.

EXAMPLE 17

1,8,9-Tri(4-methoxycarbonylbenzoyloxy)anthracene 1,8,9-Trihydroxyanthracene (2 g.), benzene (60 ml.) and pyridine (6 g.) were stirred under nitrogen until a clear solution was obtained. 4-Methoxycarbonylbenzoyl chloride (8 g.) was added in four portions during 5 minutes and the mixture was stirred for 1 hour. The solid product was collected by filtration and washed with benzene and ethanol to yield the crude product which was recrystallized (toluene - DMF 1:1) to give a yellow solid (0.9 g., 14%), m.p. 304° C. A second crop was obtained by evaporation of the reaction solution to dryness and trituration of the residue with ethanol to produce a yellow solid (1.0 g., 16%).

A sample of the first crop was adsorbed on silica gel (5 g.) from chloroform-methanol (9:1, 200 ml.) and subjected to dry column chromatography on a 20 × 1 in. column packed with Woelm dry column silica gel, which had previously been equilibrated during 3 hours with 10% w/w of chloroform-methanol 9:1. The leading component was eluted with chloroform and evaporation of the solution provided a pure sample which was characterized by the usual techniques.

By following a procedure similar to that described hereinabove in either Example 11 or Example 13 but substituting respectively for 4-methoxybenzoyl chloride and salicyloyl chloride an equivalent amount of the substituted benzoyl chlorides of Table 1 there are obtained respectively the substituted benzoyloxyanthracenes of Table 1.

By following a procedure similar to that described hereinabove in Example 14 but substituting for 2-acetoxybenzoyl chloride an equivalent amount of:
4-chlorobenzoyl chloride;
3-methylbenzoyl chloride;
2-hydroxybenzoyl chloride;
2,4-dimethylbenzoyl chloride; and,
2-acetoxy-5-chlorobenzoyl chloride,
there are obtained respectively:
mono- and di-(4-chlorobenzoyl) esters of 1,8,9-trihydroxyanthracene;
mono- and di-(3-methylbenzoyl) esters of 1,8,9-trihydroxyanthracene;
mono- and di-(2-hydroxybenzoyl) esters of 1,8,9-trihydroxyanthracene;
mono- and di-(2,4-dimethylbenzoyl) esters of 1,8,9-trihydroxyanthracene; and,
mono- and di-(2-acetoxy-5-chlorobenzoyl) esters of 1,8,9-trihydroxyanthracene.

The acid chlorides required to prepare the esters of the 1,8,9-trihydroxyanthracenes are either known in the art or can be readily prepared by methods known in the art as, for example, the method described hereinabove in Example 3 for the preparation of salicyloyl chloride.

EXAMPLE 18

Pharmaceutical formulation

The tri(2-acetoxybenzoyl)dithranol compound was made into a paste formulation suitable for topical administration. An amount equivalent to 0.2 g. dithranol (i.e., 0.64 g. ester) was admixed with 10 g. of a paste of the following composition (percentages by weight):

| | |
|---|---|
| Zinc oxide | 24% |
| Maize starch | 24% |
| White soft paraffin | 50% |
| Salicylic acid | 2% |

EXAMPLE 19

Pharmaceutical formulation

An aqueous cream formulation was made up by admixing the following ingredients (percentages by weight):

| | |
|---|---|
| Tri(2-acetoxybenzoyl)dithranol | 1.26%* |
| Emulsifying ointment (B.P.) | 30% |
| Chlorocresol | 0.1% |
| Purified water to | 100% |

*Molar concentration equivalent to 0.4% dithranol

EXAMPLE 20

Pharmaceutical formulation

Another paraffin paste formulation was made up by admixing the following ingredients (percentages by weight):

| | |
|---|---|
| Tri(2-acetoxybenzoyl)dithranol | 1.26% |
| Hard paraffin | 5% |
| Starch | 50% |
| White soft paraffin to | 100% |

Table 1

| X | Y | R' | X | Y |
|---|---|---|---|---|
| 3-F | H | H | 3-F | H |
| 2-Br | H | CH$_3$ | 2-Br | H |
| 4-I | H | H | 4-I | H |
| 3-n-C$_3$H$_7$ | H | H | 3-n-C$_3$H$_7$ | H |
| 4-t-C$_4$H$_9$ | H | H | 4-t-C$_4$H$_9$ | H |
| 4-OC$_4$H$_9$-n | H | CH$_3$ | 4-OC$_4$H$_9$-n | H |
| 4-O$_2$CC$_2$H$_5$ | H | H | 4-O$_2$CC$_2$H$_5$ | H |
| 4-CO$_2$C$_2$H$_5$ | H | H | 4-CO$_2$C$_2$H$_5$ | H |
| 2-OH | 4-OH | H | 2-OH | 4-OH |
| 3-NO$_2$ | 5-NO$_2$ | CH$_3$ | 3-NO$_2$ | 5-NO$_2$ |
| 2-CH$_3$ | 4-CH$_3$ | H | 2-CH$_3$ | 4-CH$_3$ |
| 3-CH$_3$ | 5-CH$_3$ | H | 3-CH$_3$ | 5-CH$_3$ |
| 3-OCH$_3$ | 5-OCH$_3$ | H | 3-OCH$_3$ | 5-OCH$_3$ |
| 3-O$_2$CCH$_3$ | 5-O$_2$CCH$_3$ | H | 3-O$_2$CCH$_3$ | 5-O$_2$CCH$_3$ |
| 2-CO$_2$CH$_3$ | 6-CO$_2$CH$_3$ | H | 2-CO$_2$CH$_3$ | 6-CO$_2$CH$_3$ |
| 3-OCH$_3$ | 4-CH$_3$ | CH$_3$ | 3-OCH$_3$ | 4-CH$_3$ |
| 4-CH$_3$ | 3-NO$_2$ | H | 4-CH$_3$ | 3-NO$_2$ |
| 2-Cl | 5-NO$_2$ | CH$_3$ | 2-Cl | 5-NO$_2$ |
| 3-Cl | 2-OH | H | 3-Cl | 2-OH |
| 2-OH | 3-CH$_3$ | H | 2-OH | 3-CH$_3$ |
| 2-O$_2$CCH$_3$ | 5-Cl | H | 2-O$_2$CCH$_3$ | 5-Cl |
| 2-O$_2$CCH$_3$ | 3-CH$_3$ | H | 2-O$_2$CCH$_3$ | 3-CH$_3$ |
| 2-OH | 4-OCH$_3$ | H | 2-OH | 4-OCH$_3$ |
| 3-CO$_2$CH$_3$ | 4-NO$_2$ | CH$_3$ | 3-CO$_2$CH$_3$ | 4-NO$_2$ |

EXAMPLE 21

Pharmaceutical formulation

A dusting powder formulation was made up by admixing the following ingredients (percentages by weight):

| | |
|---|---|
| Tri(2-acetoxybenzoyl)dithranol | 0.5 – 10% |
| Salicylic acid | 1 – 5% |
| Starch in powder | 5 – 10% |
| Purified talc        to | 100% |

EXAMPLE 22

Pharmaceutical formulation

An ointment formulation was made up by admixing the following ingredients (percentages by weight):

| | |
|---|---|
| Tri(2-acetoxybenzoyl)dithranol | 0.5 – 10% |
| Hydrocortisone acetate | 0.1 – 1% |
| Salicylic acid | 1 – 5% |
| Anhydrous lanolin | 10% |
| Soft paraffin        to | 100% |

EXAMPLE 23

Pharmaceutical formulation

A lotion formulation was made up by admixing the following ingredients (percentages by weight):

| | |
|---|---|
| Tri(2-acetoxybenzoyl)dithranol | 0.5 – 10% |
| Hydrocortisone – ultra fine powder | 0.1 – 1% |
| Self emulsifying monostearin | 4% |
| Chlorocresol | 0.5% |
| Glycerin | 6.3% |
| Purified water, freshly boiled and cooled        to | 100% |

In Examples 24 through 27 concentrations are given as percent by weight.

EXAMPLE 24

Pharmaceutical formulation

| | |
|---|---|
| Tri(2-acetoxybenzoyl)dithranol | 1.26% |
| Wool alcohol | 1.50% |
| Hard paraffin wax | 13.00% |
| White soft paraffin | 18.00% |
| Liquid paraffin | 22.00% |
| Water | to 100.00% |

EXAMPLE 25

Pharmaceutical formulation

| | |
|---|---|
| Di(2-acetoxybenzoyl)dithranol | 0.97% |
| Zinc Oxide | 25.00% |
| Benzoic acid | 2.00% |
| Hard paraffin wax | 6.50% |
| White soft paraffin | 56.53% |

EXAMPLE 26

Pharmaceutical formulation

| | |
|---|---|
| Di(2-acetoxybenzoyl)dithranol | 0.97% |
| Hard paraffin wax | 15.00% |
| White soft paraffin | 84.03% |

EXAMPLE 27

Pharmaceutical formulation

| | |
|---|---|
| Tri(2-acetoxybenzoyl)dithranol | 1.0% |
| White soft paraffin | 20.0% |
| Liquid paraffin | 8.0% |
| Microcrystalline wax | 10.0% |
| Lanolin | 3.0% |
| Arlacel 83 | 4.0% |
| Sorbitol syrup 70% | 2.5% |
| Distilled water | 52.5% |

Additional pharmaceutical formulations were prepared using 1.26% tri(2-acetoxybenzoyl)dithranol in the following vehicles (percentages by weight):

| Cetomacrogol Emulsifying Ointment | |
|---|---|
| Cetomacrogol 1000 | 6% |
| Cetyl alcohol | 12% |
| Stearyl alcohol | 12% |
| Liquid paraffin | 20% |
| White soft paraffin | 50% |
| Cetomacrogol Cream | |
| Cetomacrogol ointment | 30% |
| Chlorocresol | 0.1% |
| Distilled water | 69.9% |
| Carbowax | |
| Carbowax 6000 | 13% |
| PEG 400 | 87% |
| Carbowax and Cetomacrogol | |
| Carbowax 6000 | 24% |
| PEG 400 | 75% |
| Cetomacrogol 1000 | 1% |
| White Soft Paraffin | |
| White soft paraffin | 100% |

Test Results

Equivalent cream and paste formulations were prepared containing either dithranol or a substituted dithranol ester such as for example tri(2-acetoxybenzoyl)dithranol. The formulations each contained the molar equivalent of 0.4% (w/w) of dithranol. A sample of each cream and paste was applied to each of four fabrics — wool, nylon, cotton and rayon — and allowed to stand in daylight for one week. Each fabric sample was washed using detergent and a standard technique.

The fabrics treated with dithranol were very heavily stained (brown colour), but those treated with tri(2-acetoxybenzoyl) dithranol showed virtually no staining.

A subsequent experiment using tri(salicyloyl) dithranol showed slightly greater staining than the tri(2-acetoxybenzoyl) dithranol, but was still markedly superior to dithranol itself.

Pharmaceutical formulations or compositions containing the compounds of the invention are useful in treating dermatological conditions, e.g., psoriasis, comparing favorably with dithranol and chrysarobin while not having their staining and irritating properties.

I claim:

1. A compound having the formula:

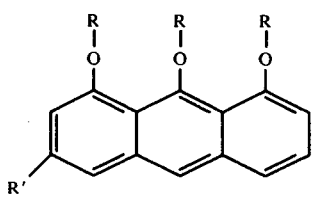

wherein:
  each R is a hydrogen atom or an X,Y-substituted-benzoyl group, at least one R being an X,Y-substituted-benzoyl group;
  X is a halogen atom, hydroxy, nitro, lower-alkyl, lower-alkoxy, phenoxy, trifluoromethyl, lower-alkylcarboxy or lower-alkoxycarbonyl;
  Y is a hydrogen atom or has the meaning given hereinabove for X, and
  R' is a hydrogen atom or a methyl group.

2. A compound according to claim 1, wherein each R is an X,Y-substituted-benzoyl group, and R' is a hydrogen atom.

3. A compound according to claim 1, wherein X or Y is a chlorine atom.

4. A compound according to claim 1, wherein X or Y is a lower-alkyl group.

5. A compound according to claim 4, wherein X or Y is a methyl group.

6. A compound according to claim 1, wherein X or Y is a lower-alkoxy group.

7. A compound according to claim 6, wherein X or Y is a methoxy group.

8. A compound according to claim 1, wherein X or Y is a phenoxy group.

9. A compound according to claim 1 wherein X or Y is a lower-alkylcarboxy group.

10. A compound according to claim 9, wherein X or Y is a methylcarboxy group.

11. A compound according to claim 1, wherein X or Y is a lower-alkoxycarbonyl group.

12. A compound according to claim 11 wherein X or Y is a methoxycarbonyl group.

13. 1,8,9-Tri(2-hydroxybenzoyloxy)anthracene according to claim 2.

14. 1,8,9-Tri(2-acetoxybenzoyloxy)anthracene according to claim 10.

15. 1,8,9-Tri(4-chlorobenzoyloxy)anthracene according to claim 3.

16. 1,8,9-Tri(3-chlorobenzoyloxy)anthracene according to claim 3.

17. 1,8,9-Tri(2-chlorobenzoyloxy)anthracene according to claim 3.

18. 1,8,9-tri(4-methylbenzoyloxy)anthracene according to claim 5.

19. 1,8,9-Tri(3-methylbenzoyloxy)anthracene according to claim 5.

20. 1,8,9-Tri(4-nitrobenzoyloxy)anthracene according to claim 2.

21. 1,8,9-Tri(3-nitrobenzoyloxy)anthracene according to claim 2.

22. 1,8,9-Tri(4-methoxybenzoyloxy)anthracene according to claim 7.

23. 1,8,9-Tri(4-hydroxybenzoyloxy)anthracene according to claim 2.

24. 1,8,9-Tri(2-hydroxybenzoyloxy)-3-methylanthracene according to claim 1.

25. The mono- or di(2-acetoxybenzoyl) esters of 1,8,9-trihydroxyanthracene according to claim 1.

26. 1,8,9-Tri(2-phenoxybenzoyloxy)anthracene according to claim 8.

27. 1,8,9-Tri[3-trifluoromethyl)benzoyloxy]anthracene according to claim 2.

28. 1,8,9-Tri[4-(methoxycarbonyl)benzoyloxy]anthracene according to claim 12.

29. A pharmaceutical composition effective in causing the temporary remission of psoriatic lesions which comprises an anti-psoriatic effective amount of an anthracene derivative according to claim 1 in combination with a pharmaceutically acceptable vehicle.

30. A composition according to claim 29 wherein in the anthracene derivative each R is an X,Y-substituted-benzoyl group and R' is a hydrogen atom.

31. A composition according to claim 30 which contains from 0.05 to 10 percent by weight of the anthracene derivative.

32. A composition according to claim 31 wherein the anthracene derivative is 1,8,9-tri-(2-acetoxybenzoyloxy)anthracene.

33. A composition according to claim 31 wherein the anthracene derivative is 1,8,9-tri-(2-hydroxybenzoyloxy)anthracene.

34. A composition according to claim 31 which additionally contains one or two ingredients selected from the group consisting of salicylic acid and hydrocortisone.

35. A method of treating psoriasis which comprises topically administering to an area of skin having psoriatic lesions a therapeutically effective amount of a composition according to claim 29.

36. A method of treating psoriasis which comprises topically administering to an area of skin having psoriatic lesions a therapeutically effective amount of a composition according to claim 32.

37. A method of treating psoriasis which comprises administering to an area of skin having psoriatic lesions a therapeutically effective amount of a composition according to claim 33.

* * * * *

UNITED STATES PATENT AND TRADEMARK OFFICE
CERTIFICATE OF CORRECTION

PATENT NO. : 4,007,271
DATED : February 8, 1977
INVENTOR(S) : Andrew Robertson

It is certified that error appears in the above-identified patent and that said Letters Patent are hereby corrected as shown below:

In the title on the face page of the patent and in column 1, "DERMATALOGICAL" should read -- DERMATOLOGICAL --.

Column 1, line 28, "dihydroxy3-" should read --dihydroxy-3- --.

Column 3, line 27, "heterocylic" should read --heterocyclic--.

Column 3, line 54, "petroluem" should read --petroleum--.

Column 5, line 39, "755/25" should read --75/25--.

Column 5, lines 54 and 55, "acetylsalicyclic" should read --acetylsalicylic--.

Column 16, Claim 27, "[3-trifluoromethyl)" should read --[3-(trifluoromethyl)--.

Signed and Sealed this

Thirteenth Day of November 1979

[SEAL]

Attest:

RUTH C. MASON
Attesting Officer

LUTRELLE F. PARKER
Acting Commissioner of Patents and Trademarks